(12) United States Patent
Emerson et al.

(10) Patent No.: US 6,350,882 B1
(45) Date of Patent: Feb. 26, 2002

(54) SYNTHESIS OF SUBSTITUTED PROLINES

(75) Inventors: Khateeta Emerson, Jersey City; Guo-Jie Ho, Scotch Plains, both of NJ (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 09/566,220

(22) Filed: May 5, 2000

Related U.S. Application Data

(60) Provisional application No. 60/135,247, filed on May 21, 1999.

(51) Int. Cl.$^7$ .............................................. C07D 207/08
(52) U.S. Cl. ........................................................ 548/533
(58) Field of Search .................................. 548/533, 535

(56) References Cited

U.S. PATENT DOCUMENTS 5,789,597 A * 8/1998 Serra Mortes et al. ...... 546/238

OTHER PUBLICATIONS

Tetrahedron Ltrs., vol. 37, No. 24, pp. 4091–4094 (1996), by P. Waid, et al.
J. Org. Chem., vol. 55, pp. 270–275 (1990), by J. Chung, et al.
Tetrahedron Ltrs., vol. 38, No. 1, pp. 89–92 (1997), by E. Lorthiois, et al.
Tetrahedron Ltrs., vol. 38, No. 1, pp. 85–88 (1997), by P. Karoyan, et al.
J. Org. Chem., vol. 61, pp. 202–209 (1996), by R. Sharma, et al.
J. Org. Chem., vol. 62, pp. 765–770 (1997), by N. Sasaki, et al.
J. Org. Chem., vol. 61, pp. 3520–3530 (1996), by M. Yamaguchi, et al.

* cited by examiner

*Primary Examiner*—T. A. Solola
*Assistant Examiner*—Sonya Wright
(74) *Attorney, Agent, or Firm*—Dianne Brown; Mark R. Daniel

(57) ABSTRACT

The instant invention is directed to a process for synthesizing substituted prolines, in particular, optically pure substituted prolines, which comprises the steps of:
a) adding an unsubstituted or substituted proline alkali salt and an alkali halide to a solution of dialkylacylamidomalonate; and
b) adding α, β unsaturated aldehyde to produce an adduct.

42 Claims, No Drawings

SYNTHESIS OF SUBSTITUTED PROLINES

DOMESTIC PRIORITY CLAIM

The priority of U.S. Provisional Application No. 60/135,247, filed on May 21, 1999, now abandoned, is claimed under 35 U.S.C. §119(e).

BACKGROUND OF THE INVENTION

Substituted prolines are widely used in biological activity studies of modified conformational constrained peptides (R. Sharma et al., *J. Org. Chem.*, Vol. 61, p. 202 (1996)). Several routes have been developed to synthesize these conformational constrained amino acid analogues (Sasaki et al., *J. Org. Chem.*, Vol. 62, p. 765, (1997); Karaoyan et al., *Tetra. Lett.*, Vol. 38, p. 85 (1997); Lorthios et al., *Tetra. Lett.*, Vol. 38, p. 89, (1997)). However, few of these routes are amenable to large-scale preparation.

Racemic 3-substituted prolines have been synthesized by condensation of diethyl acetylaminomalonate with the appropriate α, β-unsaturated aldehyde, followed by reduction, saponification, decarboxylation, and hydrolysis. (D. A. Cox et al., *J. Am. Chem. Soc.*, Vol. 88, pg. 2019 (1996); O. Tiba et al., *Polym. Sci., Part A: Polym. Chem.*, Vol. 25, pg. 3437, (1987); J. Y. L. Chung et al., *J. Org. Chem.*, Vol. 55, p. 270 (1990)). Enantiopure 3-alkyl and 3-phenylprolines were obtained through separation of the diastereomeric amides by column chromatography, followed by hydrolysis. (J. Y. L. Chung et al., *J. Org. Chem.*) This synthesis required many steps and the overall yields are low. The conjugated addition of stabilized carbanions, in the presence of alkali salts of proline as the catalyst, to α, β-unsaturated aldehydes and ketones, has been reported to afford adducts of moderate to high enantiomeric excess ("ee") (M. Yamaguchi et al., *J. Org. Chem.*, Vol. 61, p. 3520 (1996)).

Therefore, it is an object of this invention to provide a process for the synthesis of substituted prolines that is more efficient, and less time consuming.

It is also an object of this invention to provide a process for the synthesis of enantiopure substituted prolines that would not require the use of chromatography to separate the diastereomers.

It is a further object of this invention to provide a process for the synthesis of enantiopure substituted prolines that does not use expensive chiral auxiliary and produces a better yield.

SUMMARY OF THE INVENTION

The instant invention is directed to a practical process for the synthesis of substituted prolines. In particular, this invention is related to an improved, enantioselective process for the synthesis of trans 3-alkyl prolines.

DETAILED DESCRIPTION

The instant invention is directed to a process for synthesizing substituted prolines, in particular, optically pure substituted prolines. The process of the instant invention comprises the steps of:

a) adding an unsubstituted or substituted proline alkali salt and an alkali halide to a solution of dialkylacylamidomalonate; and b) adding α, β unsaturated aldehyde to produce an adduct.

In a further embodiment, the process of the instant invention comprises the steps of:

a) adding an unsubstituted or substituted proline alkali salt and an alkali halide to a solution of dialkylacylamidomalonate;

b) adding α, β unsaturated aldehyde to produce an adduct; and c) converting the adduct to provide a substituted proline.

In an embodiment of the instant invention, the steps of converting the adduct to a substituted proline comprise:

c) mixing the adduct with trialkylsilane in a solvent;

d) adding acid and aqueous base; and e) isolating an N-acyl substituted proline.

In a further embodiment of the instant invention, the steps of converting the substituted proline to an optically pure substituted proline comprise:

f) mixing the N-acyl substituted proline with a chiral base;

g) isolating a salt of the chiral base and the N-acyl substituted proline as a crystalline solid;

h) adding aqueous base and acid; and i) isolating an optically pure substituted proline.

A fourth embodiment of the instant invention comprises the steps of:

a) adding an unsubstituted or substituted proline alkali salt and an alkali halide to a solution of dialkylacylamidomalonate;

b) adding α, β unsaturated aldehyde to produce an adduct;

c) mixing the adduct with trialkylsilane in a solvent;

d) adding an acid;

e) adding a basic solution to produce a first biphasic mixture;

f) adding a solvent and an acid to the aqueous layer of the first biphasic mixture to produce a second biphasic mixture;

g) adding aqueous base to the organic layer of the second biphasic mixture to produce a third biphasic mixture;

h) adding an acid to acidify the aqueous layer of the third biphasic mixture; and i) isolating an N-acyl substituted proline.

A further embodiment of this fourth embodiment of the instant invention further comprises the steps of:

j) mixing the N-acyl substituted proline with a chiral base;

k) isolating a salt of the chiral base and the N-acyl substituted proline as a crystalline solid;

l) dissolving the salt in an aqueous base and a solvent to produce a fourth biphasic mixture;

m) adding an acid to acidify the aqueous layer of the fourth biphasic mixture; and n) isolating an optically pure substituted proline.

A specific example of the process of the instant invention comprises the steps of:

a) adding proline lithium salt and CsF to a solution of diethylacetamidomalonate; and b) adding trans-2-pentenal to produce an adduct.

A further embodiment of the specific example of instant invention comprises the steps of:

c) mixing the adduct with triethylsilane in toluene;

d) adding an inorganic acid;

e) adding a solution of $Na_2CO_3$ to produce a first biphasic mixture;

f) adding toluene and HOAc to the aqueous layer of the first biphasic mixture to produce a second biphasic mixture;

g) adding aqueous NaOH to the organic layer of the second biphasic mixture to produce a third biphasic mixture;

h) adding an acid to acidify the aqueous layer of the third biphasic mixture;

i) isolating N-acetyl-trans-3-ethylproline.

A further embodiment of the specific example of the instant invention comprises the steps of:

j) mixing the N-acetyl-trans-3-ethylproline with (S)-α-methylbenzylamine; and k) isolating a salt of (S)-α-methylbenzylamine and N-acetyl-3(R)-ethyl-2(R)-proline as a crystalline solid;

l) dissolving the salt in aqueous NaOH and MTBE to produce a fourth biphasic mixture;

m) adding an acid to acidify the aqueous layer of the fourth biphasic mixture; and n) isolating optically pure (2R,3R)-3-ethylproline.

As used herein, the phrase "substituted proline" is intended to include a proline, substituted with 1 to 3 substituents selected from an alkyl, alkoxy, aryl, aralkyl, heteroalkyl, heteroaryl or heteroaralkyl group. As used herein, "alkyl" is intended to include both branched and straight-chain saturated aliphatic hydrocarbon groups having 1 to 6 carbon atoms, unless otherwise specified; "alkoxy" represents an alkyl group of 1 to 6 carbon atoms, unless otherwise indicated, attached through an oxygen bridge. "Heteroalkyl", as used herein, is intended to refer to an alkyl chain, as described above, wherein 1 to 3 of the carbon atoms is replaced with a heteroatom, such as S, N, O and the like. "Halide", as used herein, means fluoride, chloride, bromide or iodide. As used herein, "alkali" is intended to include all of the alkali metals, such as lithium, sodium, potassium, rubidium, cesium and francium.

As used herein, "aryl" is intended to mean any stable monocyclic or bicyclic carbon ring of up to 7 members in each ring, wherein at least one ring is aromatic. Examples of such aryl elements include phenyl, naphthyl, tetrahydronaphthyl, indanyl, biphenyl, phenanthryl, anthryl or acenaphthyl.

As used herein, the terms "substituted $C_1-C_6$ alkyl" and "substituted $C_1-C_6$ alkoxy" are intended to include the branch or straight-chain alkyl group of the specified number of carbon atoms, wherein the carbon atoms may be substituted with F, Cl, Br, I, $CF_3$, $N_3$, $NO_2$, $NH_2$, oxo, —OH, —O($C_1-C_6$ alkyl), $S(O)_{0-2}$, ($C_1-C_6$ alkyl)$S(O)_{0-2}$—, ($C_1-C_6$ alkyl)$S(O)_{0-2}$($C_1-C_6$ alkyl)—, $C_3-C_{20}$ cycloalkyl, $C_2-C_6$ alkenyl, $C_2-C_6$ alkynyl, —C(O)NH, ($C_1-C_6$ alkyl)C(O)NH—, $H_2N$—C(NH)—, ($C_1-C_6$ alkyl)C(O)—, —O ($C_1-C_6$ alkyl)$CF_3$, ($C_1-C_6$ alkyl)OC(O)—, ($C_1-C_6$ alkyl)O($C_1-C_6$ alkyl)—, ($C_1-C_6$ alkyl)C(O)$_2$($C_1-C_6$ alkyl)—, ($C_1-C_6$ alkyl)OC(O)NH—, aryl, benzyl, heterocycle, aralkyl, heteroaralkyl, halo-aryl, halo-benzyl, halo-heterocycle, cyano-aryl, cyano-benzyl and cyano-heterocycle.

As used herein, the terms "substituted aryl" is intended to include the cyclic group containing from 1 to 3 substitutents in addition to the point of attachment to the rest of the compound. Such substitutents are preferably selected from the group which includes but is not limited to F, Cl, Br, I, $CF_3$, $NH_2$, $N(C_1-C_6$ alkyl)$_2$, $NO_2$, CN, $N_3$, $C_1-C_{20}$ alkyl, $C_1-C_6$ alkoxy, $C_3-C_{20}$ cycloalkyl, —OH, —O($C_1-C_6$ alkyl), $S(O)_{0-2}$, ($C_1-C_6$ alkyl)$S(O)_{0-2}$—, ($C_1-C_6$ alkyl)$S(O)_{0-2}$($C_1-C_6$ alkyl)—, ($C_1-C_6$ alkyl)C(O)NH—, $H_2N$—C(NH)—, ($C_1-C_6$ alkyl)C(O)—, ($C_1-C_6$ alkyl)OC(O)—, ($C_1-C_6$ alkyl)O ($C_1-C_6$ alkyl)—, ($C_1-C_6$ alkyl)C(O)$_2$ ($C_1-C_6$ alkyl)—, ($C_1-C_6$ alkyl)OC(O)NH—, aryl, aralkyl, heteroaryl, heteroaralkyl, halo-aryl, halo-aralkyl, halo-heterocycle, halo-heteroaralkyl, cyano-aryl, cyano-aralkyl, cyano-heterocycle and cyano-heteroaralkyl.

As used herein, "aralkyl" is intended to mean an aryl moiety, as defined above, attached through a $C_1-C_6$ alkyl linker, where alkyl is defined above. Examples of aralkyls include, but are not limited to, benzyl, naphthylmethyl and phenylbutyl.

As used herein, "heteroaralkyl" is intended to mean a heteroaryl moiety, as defined below, attached through a $C_1-C_6$ alkyl linker, where alkyl is defined above. Examples of heteroaralkyls include, but are not limited to, 2-pyridylmethyl, 2-morpholinylethyl, 2-imidazolyl-ethyl, 2-quinolinylmethyl, 2-imidazolylmethyl, 1-piperazineethyl, and the like.

The term heterocycle or heterocyclic, as used herein, represents a stable 5- to 7-membered monocyclic or stable 8- to 11-membered bicyclic heterocyclic ring which is either saturated or unsaturated, and which consists of carbon atoms and from one to four heteroatoms selected from the group consisting of N, O, and S, and including any bicyclic group in which any of the above-defined hetero-cyclic rings is fused to a benzene ring. The heterocyclic ring may be attached at any heteroatom or carbon atom which results in the creation of a stable structure. Examples of such heterocyclic elements include, but are not limited to, azepinyl, benzimidazolyl, benzisoxazolyl, benzofurazanyl, benzopyranyl, benzothiopyranyl, benzofuryl, benzothiazolyl, benzothienyl, benzoxazolyl, benzopyrazolyl, chromanyl, cinnolinyl, dibenzofuranyl, dihydrobenzofuryl, dihydrobenzothienyl, dihydrobenzothiopyranyl, dihydrobenzothiopyranyl sulfone, furyl, imidazolidinyl, imidazolinyl, imidazolyl, indolinyl, indolyl, isochromanyl, isoindolinyl, isoquinolinyl, isothiazolidinyl, isothiazolyl, isothiazolidinyl, morpholinyl, naphthyridinyl, oxadiazolyl, 2-oxoazepinyl, 4-oxonaphthyridinyl, 2-oxopiperazinyl, 2-oxopiperdinyl, 2-oxopyrrolidinyl, 2-oxopyridyl, 2-oxoquinolinyl, piperidyl, piperazinyl, pyridyl, pyridinyl, pyrazinyl, pyrazolidinyl, pyrazolyl, pyridazinyl, pyrimidinyl, pyrrolidinyl, pyrrolyl, quinazolinyl, quinolinyl, quinoxalinyl, tetrahydrofuryl, tetrahydroiso-quinolinyl, tetrahydroquinolinyl, thiamorpholinyl, thiamorpholinyl sulfoxide, thiazolyl, thiazolinyl, thienofuryl, thienothienyl, thienyl and triazolyl.

As used herein, "heteroaryl" is intended to mean any stable monocyclic or bicyclic carbon ring of up to 7 members in each ring, wherein at least one ring is aromatic and wherein from one to four carbon atoms are replaced by heteroatoms selected from the group consisting of N, O, and S. Examples of such heteroaryl elements include, but are not limited to, benzimidazolyl, benzisoxazolyl, benzofurazanyl, benzopyranyl, benzothiopyranyl, benzofuryl, benzothiazolyl, benzothienyl, benzoxazolyl, chromanyl, cinnolinyl, dihydrobenzofuryl, dihydrobenzothienyl, dihydro-benzothiopyranyl, dihydrobenzothiopyranyl sulfone, furyl, imidazolyl, indolinyl, indolyl, isochromanyl, isoindolinyl, isoquinolinyl, isothiazolyl, naphthyridinyl, oxadiazolyl, pyridyl, pyridinyl, pyrazinyl, pyrazolyl, pyridazinyl, pyrimidinyl, pyrrolyl, quinazolinyl, quinolinyl, quinoxalinyl, tetrahydroisoquinolinyl, tetrahydroquinolinyl, thiazolyl, thienofuryl, thienothienyl, and thienyl.

As used herein, a "biphasic mixture" is intended to mean a mixture containing two layers, an organic layer and an aqueous layer.

Abbreviations used throughout the specification include:

| | |
|---|---|
| Ac | Acetyl |
| ACN | acetonitrile |
| $Ac_2O$ | acetic anhydride; |
| Boc | t-Butoxycarbonyl; |

| | -continued |
|---|---|
| CBz | Carbobenzyloxy; |
| DBU | 1,8-diazabicyclo[5.4.0]undec-7-ene; |
| DEAD | diethylazodicarboxylate |
| DEM | diethoxymethane |
| DIAD | diisopropylazodicarboxylate |
| DIEA | diisopropylethylamine |
| DPAD | dipiperidineazodicarbonyl |
| DMA | N,N-dimethylacetamide |
| DMAP | 4-Dimethylaminopyridine; |
| DME | 1,2-Dimethoxyethane; |
| DMF | Dimethylformamide; |
| DMPU | 1,3-Dimethyl-3,4,5,6-tetrahydro-2-(1H)-pyrimidinone |
| DMSO | Dimethyl sulfoxide |
| EDC | 1-(3-dimethylaminopropyl)-3-ethyl-carbodiimide-hydrochloride; |
| $Et_3N$ | Triethylamine; |
| EtOAc | Ethyl acetate; |
| FAB | Fast atom bombardment; |
| HMTA | Hexamethylenetetramine |
| HOAc | Acetic acid |
| HOBT | 1-Hydroxybenzotriazole hydrate; |
| HOOBT | 3-Hydroxy-1,2,2-benzotriazin-4(3H)-one; |
| HPLC | High-performance liquid chromatography; |
| MCPBA | m-Chloroperoxybenzoic acid; |
| MEK | Methyl ethyl ketone |
| MIBK | Methyl isobutyl ketone |
| MSA | Methanesulfonic acid; |
| MsCl | Methanesulfonyl chloride; |
| MsOH | methanesulfonic acid |
| MTBE | methyl-t-butyl-ether |
| NaHMDS | Sodium bis(trimethylsilyl)amide; |
| NMP | N-Methyl pyrrolidinone |
| ODCB | Ortho Dichlorobenzene, or 1,2-dichlorobenzene |
| Py | Pyridine; |
| TFA | Trifluoroacetic acid; |
| THF | Tetrahydrofuran; |
| TsOH | P-Toluenesulfonic acid. |

SYNOPSIS OF THE SCHEMES

Schemes 1–5 illustrate the synthetic routes used in the instant invention to produce optically pure substituted prolines.

Schemes 1 and 2 depict a chiral Michael addition which establishes the stereochemistry at C-3. This is followed by reduction, hydrolysis and decarboxylation which produces a cis/trans mixture. Saponification of the cis/trans mixture isolates the trans acid.

Schemes 3–5 illustrate the synthesis of the enantiopure proline salt, using the trans acid and a chiral base. Treating the salt with base, followed by acid, yields the optically pure substituted proline.

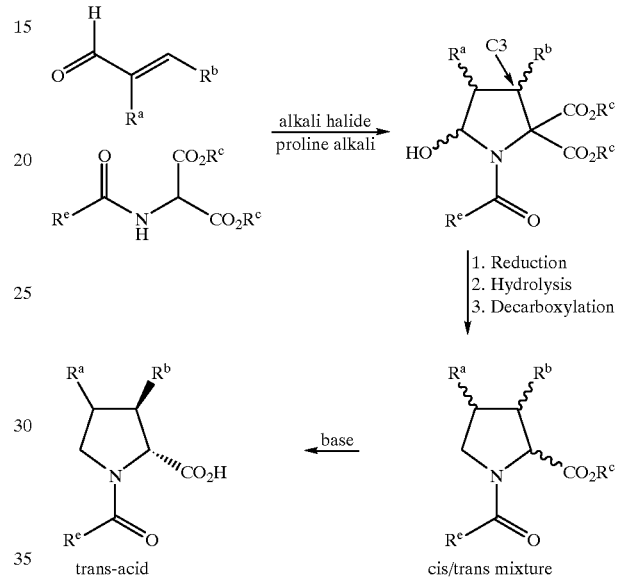

SCHEME 1

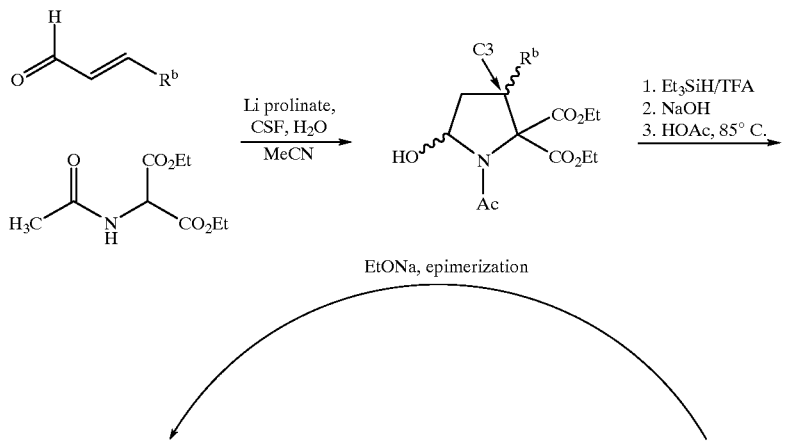

SCHEME 2

-continued

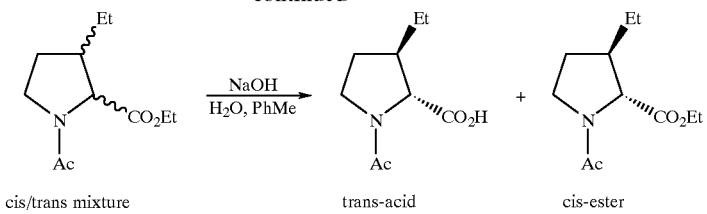

cis/trans mixture     trans-acid     cis-ester

SCHEME 3

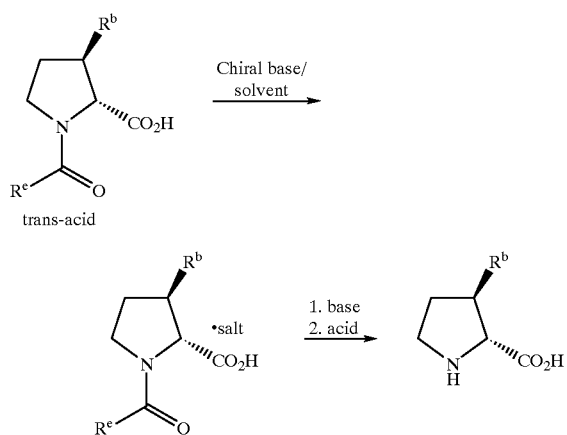

trans-acid

SCHEME 4

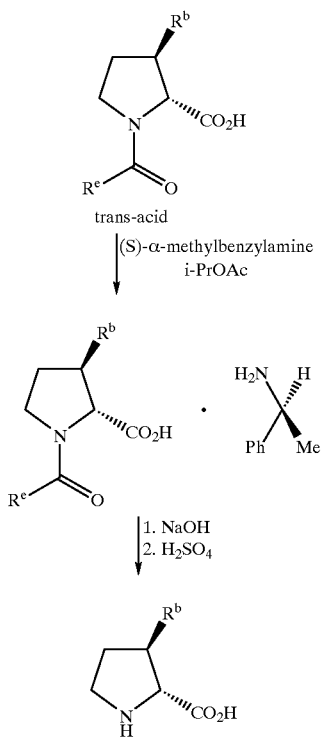

SCHEME 5

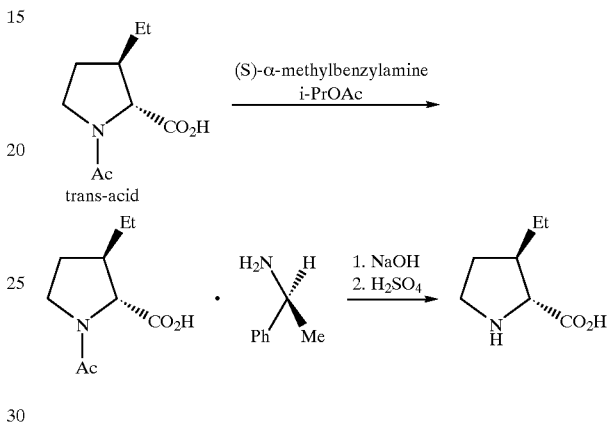

In the above Schemes, it is understood that $R^a$ and $R^b$ independently represent H, $C_1$–$C_8$ alkyl, aryl, aralkyl, heteroalkyl, heteroaryl, or heteroaralkyl; $R^c$ independently represents $C_1$–$C_8$ alkyl, aryl, or aralkyl; and $R^e$ independently represents $C_1$–$C_8$ alkyl, aryl, aralkyl, t-BOC or CBz.

Types of solvents that may be used in the instant process include, but are not limited to, water, alcohols, unchlorinated or chlorinated hydrocarbons, nitrites, ketones, ethers, esters, polar aprotic solvents or mixtures thereof Types of alcohols that can be used include, but are not limited to, methanol, ethanol, n-propanol, i-propanol, butanol or an alkoxyethanol. Types of unchlorinated hydrocarbons include, but are not limited to, toluene or xylene. Types of chlorinated hydrocarbons include, but are not limited to, dichloromethane, chloroform, chlorobenzene or ODCB. Types of nitrites include, but are limited to, acetonitrile, propionitrile, benzonitrile or tolunitrile. Types of ketones include, but are not limited to, acetone, MEK, MIBK and cyclohexanone. Types of ethers include, but are not limited to, diethyl ether, MTBE, THF, DME and DEM. Types of polar aprotic solvents include, but are not limited to, formamide, DMF, DMA, NMP, DMPU, DMSO, and sulfolane.

Types of acids which may be utilized in this process include, but are not limited to, anhydrous or aqueous organic or inorganic acids. Types of inorganic acids include, but are not limited to, HCl, HBr, HI, HF, sulfuric, phosphoric, MsOH, TsOH, or ammonium halides. Types of organic acids include, but are not limited to, acetic acid, propionic acid, TFA, MSA, citric acid, tartaric acid, other carboxylic acids and the like.

The instant invention is related to a process for the synthesis of enantiopure substituted prolines. The first step in this process requires adding an unsubstituted or substituted proline alkali salt and an alkali halide to a solution of a dialkylacylamidomalonate. Types of unsubstituted proline alkali salts include, but are not limited to, proline cesium salt, proline rubidium salt, or proline lithium salt. Types of substituted proline alkali salts include, but are not limited to, a proline alkali salt as described above, that is substituted with 1 to 3 substituents selected from alkyl, alkoxy, aryl, aralkyl, heteroaryl, or heteroalkyl. Preferably, an unsubstituted proline alkali salt, selected from proline cesium salt, proline rubidium salt, or proline lithium salt, is utilized. Most preferably, L-proline lithium salt is utilized. Preferably, the alkali halide is selected from CsF, CsCl, CsBr, RbCl, RbBr, LiCl or LiBr. Most preferably, CsF, as the alkali halide, and acetonitrile, as the solvent, are utilized. The addition of CsF in many cases resulted in an increase in enantioselectivity. Types of dialkylacylamidomalonates that may be utilized in the instant invention include, but are not limited to, diethyl-acetamidomalonate, dimethylacetamidomalonate, diethyl-2-[N-(t-butoxycarbonyl)amino] malonate or diethyl-2-[N-(carbobenzyloxyamino]malonate. Preferably, diethylacetamidomalonate is utilized. This reaction may be conducted at a temperature between about 5° C. and about 45° C. Preferably, water is present in the solution of dialkylacylamido-malonate. It should be noted that an excess amount of water may diminish the enantioselectivity of the reaction. More preferably, about 10 mol % to about 60 mol % of water is present in the solution. Next, an α, β-unsaturated aldehyde is added to produce an adduct. Types of α, β-unsaturated aldehydes that may be utilized in the instant invention include, but are not limited to, trans 2-pentenal, trans 2-hexenal, 3-methyl-2-butenal, and trans cinnamaldehyde. Preferably, trans 2-pentenal is utilized.

In a preferred embodiment of the instant invention, the adduct is obtained by using about 20 mol % of proline lithium salt and CsF as the catalysts in the presence of about 30 mol % to about 50 mol % of water. Then, preferably, trans 2-pentenal is added. This reaction is conducted for about 3 hours and, under these optimal conditions, obtains an 88% isolated yield of a mixture of the cis and trans isomers of the adduct with 62% ee. This adduct may be converted, as described below, to provide an optically pure substituted proline.

Next, the adduct is reduced by mixing it with a trialkylsilane in a solvent, which is selected from the group previously described. Types of trialkylsilanes that may be utilized in the instant invention include, but are not limited to, triethylsilane, triphenylsilane, or tripropylsilane. Preferably, triethylsilane is used. Most preferably, triethylsilane in toluene is mixed with the product. An acid, as described previously, is added next. Preferably, an organic acid is used. Most preferably, TFA is utilized in this step.

After the addition of the acid, hydrolysis is completed by adding a basic solution to produce a first biphasic mixture. Types of basic solutions that may be utilized in the instant invention include, but are not limited to, solutions containing sodium hydroxide, sodium carbonate, potassium hydroxide, lithium hydroxide or lithium carbonate. Preferably, a solution of sodium carbonate is utilized. Next, after separating the aqueous and organic layers of the first biphasic mixture, a solvent and an acid, as described previously, are added to the aqueous layer of the first biphasic mixture to produce a second biphasic mixture. Preferably, the solvent is selected from toluene, EtOAc, isopropyl acetate, MTBE or dichloromethane, and the acid is an organic acid. Most preferably, toluene and HOAc are utilized.

Next, the aqueous and organic layers of the second biphasic mixture are separated. An aqueous base is added to the organic layer of this second biphasic mixture to produce a third biphasic mixture. Types of bases that may be used in the instant process include, but are not limited to, sodium hydroxide, lithium hydroxide, potassium hydroxide, sodium carbonate, lithium carbonate or potassium carbonate. Preferably, aqueous sodium hydroxide is utilized. Next, the aqueous layer of the third biphasic mixture is separated from the organic layer and is acidified, using an acid, as described previously, to isolate an N-acyl substituted proline. Preferably, HCl is used. Types of N-acyl substituted prolines that may be isolated in the instant invention include, but are not limited to N-acetyl-substituted proline or N-Boc-substituted proline. Most preferably, N-acetyl-trans-3-ethylproline is isolated.

In one embodiment of the instant invention, saponification of a trans/cis mixture of N-acetyl 3-ethyl proline ethyl ester resulted in the formation of both trans and cis acids. After about 97% of the cis ester had been hydrolyzed, the ratio of the trans acid in the aqueous layer was 2:98 (determined by $^1$HNMR). If desired, the cis ester can be epimerized to regenerate the cis/trans mixture with a 25/75 ratio for higher yield, followed by the above selective saponification. The epimerization was carried out under similar conditions for cis 3-n-propyl proline described in J. Y. L. Chung et al., J. Org. Chem., Vol. 55, p. 270 (1990).

In a further embodiment of the instant invention, the N-acyl substituted proline, as described above, is mixed with a chiral base in a solvent, where the solvent is as described previously. Types of chiral bases that may be utilized in the instant invention, include but are not limited to, (S)-α-methylbenzylamine, quinine, quinidine, 2-butene, and quinoline. Most preferably, (S)-α-methylbenzylamine is utilized in this step. In one embodiment of the instant invention, the trans acid of N-acetyl 3-propyl proline ethyl (62% ee) is resolved through salt formation with (S)-(-)-α-methylbenzylamine in isopropyl acetate. The salt of the N-acyl substituted proline and the chiral base is then isolated as crystalline solid. This salt is then dissolved in an aqueous base and a solvent, as described previously, to produce a fourth biphasic mixture. Preferably the solvent is an organic solvent. Most preferably, the base is aqueous NaOH and the solvent is MTBE. Next, the aqueous layer of the fourth biphasic mixture is separated from the organic layer and is then acidified, using one of the acids previously mentioned. Preferably, an inorganic acid is used. Most preferably, $H_2SO_4$ is utilized. Finally, the optically pure substituted proline is isolated using standard techniques. More preferably, (2R,3R)-3-ethylproline or (2R,3R)-3-propylproline are isolated.

The overall yield for the instant invention is greater than about 30% before recycling the cis ester. Preferably, the overall yield is greater than about 35%. Optimally, the overall yield is greater than about 38%.

TABLE 1

Michael Addition of Diethylacetamido Malonate to trans 2-Pentenal[a]

| Entry | solvent | time (h) | ee %[b] | yield[c] |
|---|---|---|---|---|
| 1 | PhMe | 4 | 0 | 74 |
| 2 | $CH_2Cl_2$ | 3 | 32 | 88 |
| 3 | EtOAc | 3 | 39 | 88 |
| 4 | EtOH | 3 | 28 | 90 |
| 5 | MeCN | 3 | 62 | 88 |
| 6[d] | MeCN | 17 | 40 | 90 |

TABLE 1-continued

Michael Addition of Diethylacetamido Malonate to trans 2-Pentenal[a]

| Entry | solvent | time (h) | ee %[b] | yield[c] |
|-------|---------|----------|---------|----------|

[a]Reactions were carried out using 20 mol % of proline Li salt and CeF as the catalysts in the presence of 30 mol % water, see Experimental for reaction conditions.
[b]Determined using supercritical fluid chromatography (SFC). Both cis and trans isomer have the same ee.
[c]The yield refers to the isolated yield of a mixture of cis and trans isomers.
[d]Only 14 mol % of proline Li salt and 5 mol % of CeF were used.

TABLE 2

The effect of water on the Asymmetric Michael Addition in MeCN[a]

| Entry | amount H$_2$O (mol %) | time (h) | ee %[b] | yield %[c] |
|-------|----------------------|----------|---------|------------|
| 1 | <1 | 7 | 12 | 86 |
| 2 | 10 | 4 | 50 | 86 |
| 3 | 30 | 3 | 62 | 88 |
| 4 | 50 | 3 | 54 | 88 |
| 5 | 75 | 1.5 | 11 | 85 |
| 6 | 100 | 1 | 6 | 85 |

[a]Reactions were carried out using 20 mol % of proline Li salt and CeF as the catalysts. See Experimental for reaction conditions.
[b]Determined using supercritical fluid chromatography (SFC). Both cis and trans isomer have the same ee.
[c]The yield refers to the isolated yield of a mixture of cis and trans isomers.

As shown in Table 1, a high yield and enantioselectivity were obtained in a polar solvent such as acetonitrile, and this may be due to increased solubility of the catalyst, while essential to the reaction for good yield and enantiomeric excess, an excess amount of water diminished the enantioselectivity of the reaction (See Table 2). Similar effects, though not as pronounced, were also observed for other solvents. Optimal enantiomeric excess was obtained with about 30 mol % of water present. The enantiomeric excess is lower when the reaction was carried out at about 5° C., whereas similar enantiomeric excess and yield were resulted at about 20° C. and about 35° C.

Under optimal reaction conditions (entry 5, Table 1), the cyclized adduct was obtained in about 88% yield with about 62% ee. Optimally, the adduct can be reduced with Et$_3$SiH/TFA in toluene to the N-acetyl pyrrolidine diester. HPLC analysis indicated quantitative conversion with little side product formation. The crude toluene solution after reduction was subjected to hydrolysis over aqueous NaOH, allowing separation of the side products of the previous step (Et$_3$SiOH, Et$_3$SiH, etc.) from the mono acid (sodium salt). After acidification with acetic acid and decarboxylation, a mixture of the cis trans esters was obtained in a ratio of about 30/70. On the other hand, decarboxylation under anhydrous conditions would give the cis ester as the major product, which had to be epimerized to the desired trans ester prior to hydrolysis.

EXAMPLES

NMR spectra were recorded at 250 MHz using DMSO-d$_6$, D$_2$O, or CDCl$_3$ as the solvent. Chemical shifts and coupling constants are given in ppm and Hz, respectively. HPLC analysis were performed using a YMC J'sphere H80 column (4.6×250 mm) with a gradient mixture of aqueous H$_3$PO$_4$ (20 mM) and MeCN as the eluent. All chemicals were purchased from Aldrich Chemical Co. Prior to use, trans-2-pentenal was distilled under nitrogen, and others were used as received. The amino acid salts were prepared according to the literature procedure.

Enantioselectivities were determined by Hewlett Packard Supercritical Fluid Chromatography (SFC, HP 1250A) using a Chiracel OD-H (4.6×250 mm) column and methanol as the modifier in supercritical carbon dioxide (35° C.; 300 psi). The flow rate is 0.5 ml/min and the wavelength is 210 nm.

Example 1

Diethyl 1-Acetyl-5-hydroxy-3-ethylpyrrolidine-2,2-dicarboxylate

Diethylacetamido malonate 2 (10.0 g, 46 mmol) was dissolved in dry MeCN (molecular sieves, 50 mL, K.F. <50 μg/mL) and water (0.25 g, 14 mmol) was added. L-Proline Li salt (1.1 g, 9 mmol) and CsF (1.4 g, 9 mmol) were added. After stirring for 5 min, trans 2-pentenal 1 (5.8 g, 69 mmol) was added dropwise. The mixture was stirred for 3 h at 20° C., then quenched with HOAc (5 mL). After concentrated in vacuo to a volume of 10 mL, EtOAc (100 mL) was added and the mixture was concentrated again to 50 mL. The solution was washed with 1M aqueous NaHCO$_3$ (20 mL) and H$_2$O (10 mL). The organic layer was concentrated in vacuo to 25 mL and hexanes (25 mL) was added. After aging for 1 h, the mixture was filtered and the solid were washed with EtOAc/hexanes (3/7, 20 mL). The product was dried in vacuo to yield the above-titled compound. $^1$H NMR (CD$_3$OD): δ 5.65 (d, 1 H, J=5.1 Hz), 4.1–4.25 (m, 4 H), 2.7–2.7 (m, 1 H), 2.21 (s, 3 H), 2.1 (dd, 1 H, J=6.3 Hz), 1.86–1.97 (m, 2 H), 1.27 (t, 3 H, J=7 Hz), 1.23 (t, 3 H, J=7 Hz), 1.1–1.25 (m, 1 H), 0.97 (t, 3 H, J=7.4 Hz).

Example 2

Diethyl 1-Acetyl-3-ethylpyrrolidine-2-carboxylate (mixture of cis and trans isomers)

To a mixture of the dicarboxylate, as described above in Example 1, (12 g, 40 mmol) and triethylsilane (8.2 mL, 52 mmol) in toluene (120 mL), was added TFA (12.3 mL, 160 mmol) at about 0° C. to about 5° C. The solution was allowed to warm to 20° C. and stirred for 14 h. The mixture was concentrated in vacuo to 60 mL and washed with 1M aqueous Na$_2$CO$_3$ (30 mL). The resulting aqueous layer was extracted with toluene (30 mL). The combined organic extract was concentrated to 25 mL. To this solution was added 1M aqueous NaOH (120 mL) and the resulting 2-phase mixture was stirred for 16 h. After phase separation, the aqueous solution was washed with Hexanes (60 mL). Toluene (120 mL) and HOAc (14.4 g, 0.24 mol) were added and the 2-phase mixture was stirred at 85° C. for 2 h. After cooled to 20° C., the mixture was neutralized with NaHCO$_3$ to a pH of about 7, and the phases were separated. A mixture of the cis/trans isomers (1:3) was obtained as a toluene solution.

Example 3

Preparation of N-Acetyl-trans-3-ethylproline

To a toluene solution, as described above in Example 2, was added 0.3 M aqueous NaOH (100 mL), and the 2-phase mixture was stirred at 35° C. for 3 h. Additional NaOH (1 M, 10 mL) was added and the mixture was further stirred for 14 h. After phase separation, MTBE (130 mL) was added to the aqueous solution. The mixture was saturated with NaCl and acidified to a pH of about 2 with 6 N HCl. The aqueous layer was extracted with 2×40 mL of MTBE. The combined MTBE solution was washed with 40 mL of sat brine then dried over $Na_2SO_4$. Evaporation of the solvent provided the above titled compound as a white solid, with a 62% ee.

Example 4

Preparation of (2R,3R)-3-Ethylproline

Step A: Resolution Via Methylbenzylamine Salt

A mixture of N-acetyl-trans-3-ethylproline, as described in Example 3, (5.0 g; 27 mmol) and (S)-α-methylbenzylamine (3.3 g, 27 mmol) in i-PrOAc (50 mL) was stirred at 20° C. for 10 h. The solids were filtered, washed with i-PrOAc (2×10 mL). The salt of (S)-α-methylbenzyl-amine and N-acetyl-3(R)-ethyl-2(R)-proline was obtained as a crystalline solid.

$^1$H NMR ($D_2O$) δ 7.47 (br s, 5 H), 4.52 (q, J=6.9 Hz, 1 H), 3.83–3.90 (2 d's J=3.9 & 4.0 Hz, 1 H) 3.42–3.61 (m, 2 H), 2.05 (m, 4 H), 1.93 (s, 1 H), 1.63 (d, J=6.9 Hz, 3 H), 1.60–1.51 (m, 1 H), 1.42–1.31 (m, 3 H), 0.91 (m, 3 H).

Step B: Salt Break and Deprotection

The salt, as described above, (5.8 g, 19 mmol) was dissolved in 2 M aqueous NaOH (25 mL) and MTBE (25 mL) was added. The aqueous layer was separated and acidified with 9 M $H_2SO_4$ (15 mL). The resulting solution was refluxed for 3.5 h. After cooling, the solution was loaded onto an amberlyst 15 ion exchange resin column. The column was washed with water then 2N $NH_4OH$. The amino acid containing fractions (ninhydrin-positive fractions) were concentrated and flushed with 2-propanol. (2R,3R)-3-Ethylproline was obtained as a white crystalline solid after drying at 60° C. in vacuo. The ee for the (2R,3R)-3-ethylproline was greater than 99%.

$^1$H NMR (DMSO-$d_6$) δ (m, 3 H), 1.63 (d, J=6.9, 5 H), 1.93 (s, 1 H), 2.05 (m, 4 H), 3.42–3.61 (m, 2 H), 3.83–3.90 (2d, J=3.9, 1 H), 4.52 (q, J=6.9, 1 H 7.47 (s, 5H).

Example 5

Preparation of (2R,3R)-3-Propylproline

Using the procedures described in Examples 1–5, but substituting trans-2-hexenal for trans-2-pentenal, the title compound was obtained. By reacting diethylacetamido malonate with trans-2-hexenal, the corresponding Michael adduct was obtained with a 90% yield and a 54% ee. The conversion of the Michael adduct to the (2R,3R)-3-propylproline produced an overall yield of about 42%. The $^1$H NMR was identical to that in the literature. (Chung, J. Y. L., et al., J. Org. Chem., 1990, vol. 55, p. 270.)

What is claimed is:

1. A process for synthesizing substituted prolines which comprises the steps of:
 a) adding an unsubstituted or substituted proline alkali salt and an alkali halide to a solution of dialkylacylamidomalonate; and
 b) adding α, β unsaturated aldehyde to produce an adduct;
 c) mixing the adduct with trialkylsilane in a solvent;
 d) adding acid and aqueous base; and
 e) isolating an N-acyl substituted proline.

2. The process of claim 1 which further comprises the steps of converting the substituted proline to an optically pure substituted proline by:
 f) mixing the N-acyl substituted proline with a chiral base;
 g) isolating a salt of the chiral base and the N-acyl substituted proline as a crystalline solid;
 h) adding aqueous base and acid; and
 i) isolating an optically pure substituted proline.

3. The process of claim 1 which comprises the steps of:
 a) adding an unsubstituted or substituted proline alkali salt and an alkali halide to a solution of dialkylacylamidomalonate;
 b) adding α, β unsaturated aldehyde to produce an adduct;
 c) mixing the adduct with trialkylsilane in a solvent;
 d) adding an acid;
 e) adding a basic solution to produce a first biphasic mixture;
 f) adding a solvent and an acid to the aqueous layer of the first biphasic mixture to produce a second biphasic mixture;
 g) adding aqueous base to the organic layer of the second biphasic mixture to produce a third biphasic mixture;
 h) adding an acid to acidify the aqueous layer of the third biphasic mixture; and
 i) isolating an N-acyl substituted proline.

4. The process of claim 3 which further comprises the steps of:
 j) mixing the N-acyl substituted proline with a chiral base;
 k) isolating a salt of the chiral base and the N-acyl substituted proline as a crystalline solid;
 l) dissolving the salt in an aqueous base and a solvent to produce a fourth biphasic mixture;
 m) adding an acid to acidify the aqueous layer of the fourth biphasic mixture; and
 n) isolating an optically pure substituted proline.

5. The process of claim 3, wherein the unsubstituted proline alkali comprises proline cesium salt, proline rubidium salt, or proline lithium salt.

6. The process of claim 3, wherein the substituted proline alkali comprises proline cesium salt, proline rubidium salt, or proline lithium salt, which is substituted with 1 to 3 substituents comprising an alkyl, alkoxy, aryl, heteroalkyl, or heteroaryl group.

7. The process of claim 5, wherein the unsubstituted proline alkali salt is L-proline lithium salt.

8. The process of claim 3, wherein the alkali halide comprises CsF, CsCl, CsBr, RbCl, RbBr, LiCl or LiBr.

9. The process of claim 8, wherein the alkali halide is CsF.

10. The process of claim 3, wherein the dialkylacylamidomalonate comprises diethylacetamidomalonate, diethylacetamidomalonate, diethyl-2-[N-(t-butoxycarbonyl)amino]malonate or diethyl-2-[N-(carbobenzyloxyamino]malonate.

11. The process of claim 10, wherein the dialkylacylamidomalonate is diethylacetamidomalonate.

12. The process of claim 3, wherein the α, β-unsaturated aldehyde comprises trans 2-pentenal, trans 2-hexenal, 3-methyl-2-butenal, or trans cinnamaldehyde.

13. The process of claim 12, wherein the α, β-unsaturated aldehyde is trans 2-pentenal.

14. The process of claim 3, wherein the trialkylsilane comprises triethylsilane, triphenylsilane, or tripropylsilane.

15. The process of claim 14, wherein the trialkylsilane is triethylsilane.

16. The process of claim 3, wherein the solvent comprises water, alcohols, unchlorinated or chlorinated hydrocarbons, nitriles, ketones, ethers, esters, polar aprotic solvents or mixtures thereof.

17. The process of claim 16, wherein the solvent used in step c) is an unchlorinated hydrocarbon comprising toluene or xylene.

18. The process of claim 17, wherein the solvent is toluene.

19. The process of claim 3, wherein the acid comprises an anhydrous or aqueous organic or inorganic acid.

20. The process of claim 3, wherein the acid used in step d) is an organic acid comprising acetic acid, propionic acid, TFA, MSA, citric acid, tartaric acid, or other carboxylic acids.

21. The process of claim 20, wherein the organic acid is TFA.

22. The process of claim 3, wherein the basic solution comprises solutions containing sodium hydroxide, sodium carbonate, potassium hydroxide, lithium hydroxide or lithium carbonate.

23. The process of claim 22, wherein the basic solution is a solution containing sodium carbonate.

24. The process of claim 3, wherein the solvent used in step f) comprises toluene, EtOAc, isopropyl acetate, MTBE or dichloromethane.

25. The process of claim 24, wherein the solvent is toluene.

26. The process of claim 3, wherein the acid used in step f) is an organic acid comprising acetic acid, propionic acid, TFA, MSA, citric acid, tartaric acid, or other carboxylic acids.

27. The process of claim 26, wherein the acid is acetic acid.

28. The process of claim 3, wherein the aqueous base comprises sodium hydroxide, lithium hydroxide, potassium hydroxide, sodium carbonate, lithium carbonate or potassium carbonate.

29. The process of claim 28, wherein the aqueous base is sodium hydroxide.

30. The process of claim 3, wherein the acid used in step h) is an inorganic acid comprising HCl, HBr, HI, HF, sulfuric, phosphoric, MsOH, TsOH, or ammonium halides.

31. The process of claim 30, wherein the acid is HCl.

32. The process of claim 4, wherein the chiral base comprises (S)-α-methylbenzylamine, quinine, quinidine, 2-butene, or quinoline.

33. The process of claim 32, wherein the chiral base is (S)-α-methylbenzylamine.

34. The process of claim 4, wherein the aqueous base used in step l) comprises sodium hydroxide, lithium hydroxide, potassium hydroxide, sodium carbonate, lithium carbonate or potassium carbonate.

35. The process of claim 34, wherein the aqueous base is sodium hydroxide.

36. The process of claim 4, wherein the solvent used in step l) is MTBE.

37. The process of claim 4, wherein the acid used in step m) is an inorganic acid comprising HCl, HBr, HI, HF, sulfuric, phosphoric, MsOH, TsOH, or ammonium halides.

38. The process of claim 37, wherein the acid is sulfuric acid.

39. The process of claim 4, wherein the optically pure substituted proline isolated in step (n) comprises (2R,3R)-3-ethylproline or (2R,3R)-3-propylproline.

40. The process of claim 3, wherein the adduct of step (b) is produced using about 10 mol % to about 60 mol % of water.

41. The process of claim 40, wherein about 30 mol % to about 50 mol % of water is used.

42. The process of claim 3, wherein step (b) is conducted at a temperature between about 5° C. and about 45° C.

\* \* \* \* \*